United States Patent
Wang et al.

(10) Patent No.: US 7,666,293 B2
(45) Date of Patent: Feb. 23, 2010

(54) ELECTROCHEMICAL REDUCTION OF HALOGENATED 4-AMINOPICOLINIC ACIDS

(75) Inventors: Chen Wang, Midland, MI (US); Carey L. Scortichini, Midland, MI (US); Todd S. Bridson, Midland, MI (US)

(73) Assignee: Dow AgroSciences LLC, Indianapolis, IN (US)

( * ) Notice: Subject to any disclaimer, the term of this patent is extended or adjusted under 35 U.S.C. 154(b) by 111 days.

(21) Appl. No.: 11/906,859

(22) Filed: Oct. 4, 2007

(65) Prior Publication Data

US 2009/0090639 A1 Apr. 9, 2009

(51) Int. Cl.
*C25B 3/00* (2006.01)

(52) U.S. Cl. ........................... 205/426; 205/440

(58) Field of Classification Search ............... 205/426, 205/440
See application file for complete search history.

(56) References Cited

U.S. PATENT DOCUMENTS

| 3,285,925 A | 11/1966 | Johnston et al. |
| 3,694,332 A | 9/1972 | Parker |
| 4,217,185 A | 8/1980 | Kyriacou et al. |
| 4,242,183 A | 12/1980 | Kyriacou |
| 6,297,197 B1 | 10/2001 | Fields et al. |
| 6,352,635 B2 * | 3/2002 | Krumel et al. ............ 205/426 |

FOREIGN PATENT DOCUMENTS

RU 1807686 5/1994

OTHER PUBLICATIONS

International Search Report for PCT/US2007/021336 (including 2 non-US patent references), Jan. 25, 2008, Dow AgroSciences LLC [Chen Wang et al.].

* cited by examiner

*Primary Examiner*—Edna Wong
(74) *Attorney, Agent, or Firm*—Craig E. Mixan

(57) ABSTRACT

The selective electrochemical reduction of halogenated 4-aminopicolinic acids is improved by activating the cathode in the presence of the starting material, excess alkali metal hydroxide and an alkali metal chloride, bromide or sulfate.

3 Claims, No Drawings

ELECTROCHEMICAL REDUCTION OF HALOGENATED 4-AMINOPICOLINIC ACIDS

BACKGROUND OF THE INVENTION

The present invention concerns an improved process for the selective electrochemical reduction of halogenated 4-aminopicolinic acids.

U.S. Pat. No. 6,352,635 B2 describes the preparation of certain herbicidal 3-halo-4-aminopicolinic acid derivatives by the electrochemical reduction of certain 3,5-dihalo-4-aminopicolinic acid derivatives. In this process, the silver cathode is either activated by anodization in the presence of 2 percent sodium hydroxide and 1 percent sodium chloride, or anodized in the presence of starting material to be reduced and 1 to 3 weight percent of excess NaOH. Because of passivation, however, it is usually necessary to reactivate the cathode by anodization in the presence of the electrolyte to finish a batch. It would be desirable to have an improved method for activating the cathode that is more resistant to passivation.

SUMMARY OF THE INVENTION

It has now been found that, by activating the cathode in the presence of the starting material to be reduced, excess alkali metal hydroxide and 0.5 to 4 weight percent of an alkali metal chloride, bromide or sulfate, the reaction rate is faster, the current efficiency is higher and the cathode does not need to be reactivated to finish a batch. More particularly, the present invention concerns an improved process for the preparation of a 4-amino-3-halopicolinic acid of Formula I

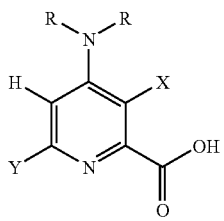

I wherein

X represents Cl or Br,

Y represents H, F, Cl, Br or $C_1$-$C_4$ alkyl, with the proviso that when X is Cl, Y is not Br, and R independently represents H or $C_1$-$C_4$ alkyl, in which a direct or alternating electric current is passed from an anode to a cathode through a solution of a 4-amino-3,5-dihalopicolinic acid of Formula II

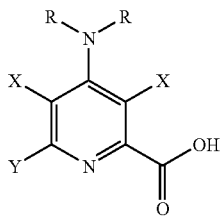

II wherein

X, Y and R are as previously defined, and wherein both of X are either Cl or Br, at a cathode potential of about −0.4 to about −1.7 volts relative to an Ag/AgCl (3.0 M Cl⁻) reference electrode, the improvement characterized by activating the cathode in the presence of the 4-amino-3,5-dihalopicolinic acid of Formula II, an excess of alkali metal hydroxide and 0.5 to 4 weight percent of an alkali metal chloride, bromide or sulfate.

DETAILED DESCRIPTION OF THE INVENTION

The present invention concerns an improved process for the selective electrochemical reduction of the 5-halo substituent of 4-amino-3,5-dihalopicolinic acids. As used herein, the term "halogen" or "halo" refers to Cl or Br. Alkali metal means lithium, sodium, potassium, rubidium and cesium with sodium and potassium being preferred.

The reactions involved in the reduction of the 4-amino-3,5-dihalopicolinic acid may be depicted as follows:

A) Neutralization:

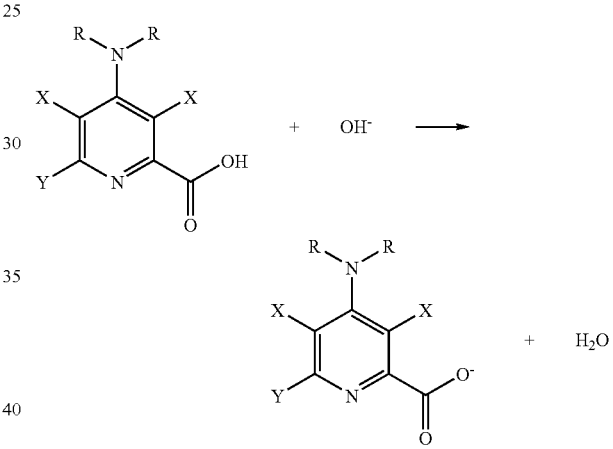

B) Cathode Reaction:

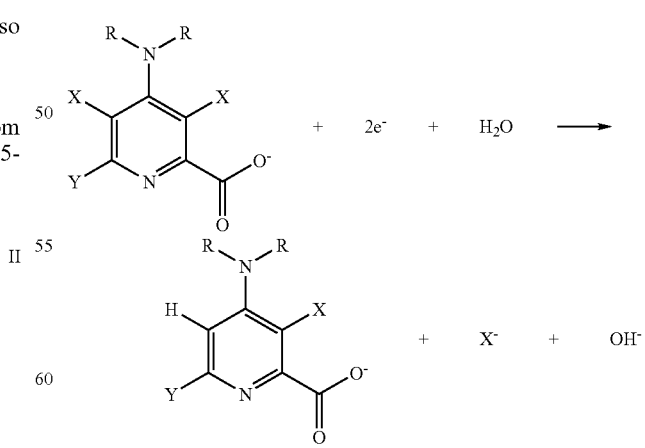

C) Anode Reaction:

$$2(OH^-) \rightarrow {}_{1/2}O_2 + H_2O + 2e^-$$

D) Overall Reaction:

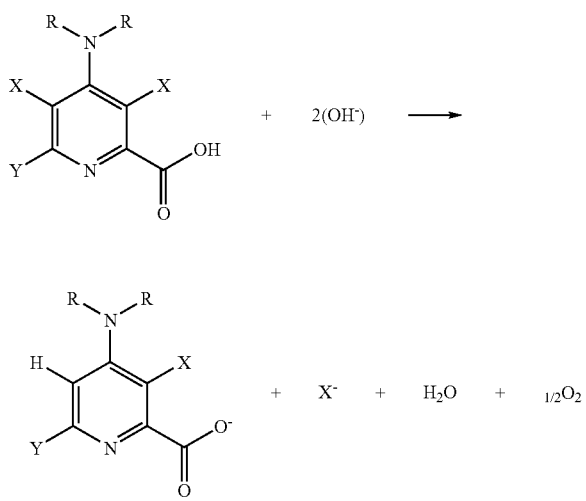

The carboxylic acid is recovered by acidifying the reaction mixture and recovering the product by conventional techniques.

The desired electrolytic reduction is carried out by techniques that are generally known in the art. In general, the starting 4-amino-3,5-dihalopicolinic acid is dissolved in a solvent to form an electrolyte which is added to the electrolytic cell while enough current is passed through the electrolyte until the desired degree of reduction is obtained.

It should be appreciated by those skilled in the art that the reduction potential of an aryl bromide is about 0.5 volt higher (less negative) than the comparable aryl chloride potential. The bromine will always be reduced off first. Thus, when X is Cl, Y cannot be Br.

The design of the electrolysis cell is flexible. The electrolysis can be conducted batch-wise, or in a continuous or semi-continuous fashion. The cell may be a stirred tank containing the electrodes or a flow cell of any conventional design. In some cases, it may be desirable to employ a separator to divide the cell into separate anodic and cathodic compartments. Examples of useful separator materials are various anion and cation exchange membranes, porous Teflon, asbestos, and glass. While the use of three electrodes in which the potential of the cathode is controlled relative to a reference electrode is preferred, the electrolysis can alternatively be performed using only two electrodes, an anode and a cathode, and controlling either the cell current, the cell voltage, or both. For convenience, a 3-electrode undivided cell in which the electrolyte serves as both the catholyte and the analyte is preferred.

The anode can be any chemically inert material including, for example, platinum, graphite, carbon, metal oxides such as silver oxide on silver, or alloys such as Hastelloy C, with graphite, carbon and Hastelloy C being preferred. The cathode is primarily constructed of silver. Electrodes may be in the form of plates, rods, wires, screens, gauze, wool, sheets or pools, with expanded mesh screens being preferred. The anode or cathode may also consist of a coating applied to another material, an example of which is a noble metal oxide such as ruthenium oxide coated onto titanium.

The most preferred cathodes are activated silver cathodes prepared as described in U.S. Pat. Nos. 4,217,185 and 4,242,183. Such activated cathodes can be prepared by depositing a layer of silver microcrystals on a conductive substrate to form a composite electrode or by anodization of a silver electrode itself. For example, to illustrate the latter, an unactivated silver electrode can be dipped or immersed in an aqueous caustic catholyte solution and anodized, thus converting some of the silver at the surface of the electrode to silver oxide and roughening the surface at the same time. The polarity of the electrode is then reversed and the oxide electrolytically converted into particles of microcrystalline silver adhered to the surface of the electrode. The activation procedure involves increasing the potential from an initial value of zero volts to a final value of at least +0.3 volts and preferably about +0.7 volts. Reduction of the oxide deposit requires negative polarization of the cathode. The cathode potential is gradually reduced from the value of about +0.3 to about +0.7 volts attained during the oxidation step, to a value of about −0.5 volts or less. It is not necessary to add any silver to the catholyte or aqueous base in this method.

Typically, the cathode is activated in the presence of from about 0.5 to about 4 wt % of an alkali metal chloride, bromide or sulfate, preferably NaCl, an excess of alkali metal hydroxide, preferably from about 1.0 to about 4.0 wt % NaOH, and the additional presence of the starting material to be reduced. Conveniently, the starting material is present in the same concentration as it is in the reaction feed, i.e., from about 1 to about 20 wt %, preferably from about 8 to about 12 wt %. This improvement is particularly advantageous for the production of 4-amino-3,6-dichloropyridine-2-carboxylic acid (aminopyralid) from 4-amino-3,5,6-trichloropyridine-2-carboxylic acid (picloram).

Water is the most preferred solvent for the electrolysis but, in some circumstances, it is possible to use an organic solvent either alone or as a co-solvent. The solvent or the co-solvent system should dissolve all or most of the starting material and the electrolyte, or at least enough to allow the reduction to proceed at a reasonable rate. In addition, the solvent or the co-solvent system should be inert to the electrolysis conditions, i.e., it does not detrimentally alter or react with the cathode or the catholyte materials to an intolerable extent. Other than water, preferred solvents/co-solvents are miscible with water and include lower molecular weight alcohols, ethers such as tetrahydrofuran, dioxane and polyglycol ethers, and lower amides such as dimethyl formamide or dimethyl acetamide.

Alkali metal hydroxides are needed as the supporting electrolyte and NaOH and KOH are the most preferred supporting electrolytes. While NaCl is the preferred salt, other salts can be used include alkali chlorides, bromides, and sulfates.

In the reaction, one equivalent of base is required to neutralize the starting material and an additional equivalent is required to generate hydroxyl ions that are consumed in the electrolysis. The reaction is typically run with an excess of base, preferably with a 1 to 4 weight percent excess of base throughout the reaction.

The concentration of halogenated 4-aminopicolinic acid in the catholyte or feed can be from about 1 to about 20 percent by weight, preferably from about 8 to about 12 percent by weight. Lower concentrations reduce productivity while higher concentrations usually result in lower yields, lower product purity and lower electrical efficiencies.

Suitable temperatures for the electrolysis generally range from about 5 to about 90° C. The preferred temperature range is from about 20 to about 60° C. From about 30 to about 50° C. is most preferred.

One skilled in the art will appreciate that the apparent cathode potential at which the halogen will be selectively reduced, is dependent on a variety of factors including, for example, the structure of the particular substrate, the cell configuration, and the distance separating the electrodes. In general, the cathode potential, relative to a standard Ag/AgCl (3.0 M Cl$^-$) electrode, should be within the range of about −0.4 to about −1.1 volts for Br and within the range of about −0.8 to about −1.7 volts for Cl. For Br, the cathode potential is preferably from about −0.6 to about −0.9 volts. For Cl, the cathode potential is preferably from about −1.0 to about −1.4 volts. The current density in amperes per square centimeter (amp/cm$^2$) should be at least 0.005, preferably about 0.05 amp/cm$^2$ or greater.

While the evolution of molecular oxygen is preferred, many other anodic reactions can be employed. Examples include the evolution of molecular chlorine or bromine, oxidation of a sacrificial species such as formate or oxalate to give carbon dioxide, or the oxidation of an organic substrate to form a valuable co-product.

In the presently preferred mode of operation, a halogenated 4-aminopicolinic acid is dissolved in aqueous caustic brine to form a basic aqueous solution (~10 wt % halogenated 4-aminopicolinic acid, ~2.5 wt % excess NaOH and ~1 wt % NaCl) which is continuously recirculated through an undivided electrochemical cell having an expanded silver mesh cathode activated by anodization at +0.7 volts in the presence of the feed solution. While keeping the reaction mixture alkaline, electrolysis at a cathode potential of from about −0.6 to about −1.5 volts relative to an Ag/AgCl (3.0 M Cl$^-$) reference electrode is continued until the desired degree of reduction has occurred. The desired product is recovered by conventional techniques. For example, the acid can be precipitated from the reaction mixture by acidification followed by either filtration or extraction with a water immiscible organic solvent.

The following examples are illustrative of the present invention.

EXAMPLES

Example 1

Comparative Example

Preparation of
4-amino-3,6-dichloropyridine-2-carboxylic acid
(batch cell in presence of starting material and
NaOH during activation)

To a 4-liter (L) flask was added 2400 grams (g) of hot water, 250 g of 50 percent by weight NaOH, and 350 g of wet 4-amino-3,5,6-trichloropyridine-2-carboxylic acid (80 percent). The solution was stirred for 30 minutes (min), filtered through a 1 micron polypropylene film, and transferred to a 5-L feed circulation tank. This solution weighed 3000 g and contained 9.3 percent 4-amino-3,5,6-trichloropyridine-2-carboxylic acid and 2.0 to 2.5 percent of excess NaOH.

This feed solution was circulated at a rate of 18 L/min and a temperature of 35-38° C. through two undivided electrochemical cells in series. Each cell had a Hastelloy C anode (17.5 cm×5.6 cm) and an expanded silver mesh cathode (17.5 cm×5.6 cm). Only one of the two cells was controlled and monitored electrically. After normal anodization at +0.7 volts (V), the polarity of the cell was reversed and the electrolysis was started. The cathode working potential was controlled at −1.1 to −1.4 V relative to an Ag/AgCl (3.0 M Cl—) reference electrode. The reference electrode was physically located directly behind the silver cathode and connected electrically with an aqueous salt bridge. While recirculating the feed, 160 g of 50 percent by weight NaOH was slowly pumped into the recirculation tank over 6 hours to maintain the NaOH concentration at 1.5-3.0 percent excess. The current ranged from 0.5 to 7.0 amps.

Anodization and reversion were repeated at 8 hours and 24 hours into the electrolysis respectively. After about 36 hours and 249,000 coulombs had been passed through the controlled cell, the electrolysis was terminated and the cell effluent was released to another 5 L flask and was neutralized with concentrated HCl. The total weight of the neutralized solution was about 3200 g. About 1000 grams of the solution was concentrated in vacuo to 750 g of crude concentrate. The concentrate was warmed to 85° C. while stirring and pH was adjusted to 0.8-1.1 with concentrated HCl over 30 min. The resulting slurry was cooled to ambient temperature and filtered. The filter cake was washed with 40 g of water three times, and dried in oven at 70° C. for 10 hours. The dried product weighed at 62 g with an assay of 95 percent desired product. High Pressure Liquid Chromatography analysis of the dried product indicated about 2 percent of the starting material remaining as an impurity.

Example 2

Comparative Example

Preparation of
4-amino-3,6-dichloropyridine-2-carboxylic acid
(batch cell in presence of NaOH and NaCl only
during activation)

To a 4-liter (L) flask was added 2400 grams (g) of hot water, 250 g of 50 percent by weight NaOH, and 350 g of wet 4-amino-3,5,6-trichloropyridine-2-carboxylic acid (80 percent). The solution was stirred for 30 minutes (min), filtered through a 1 micron polypropylene film, and transferred to a 5-L feed circulation tank. This solution weighed 3000 g and contained 9.3 percent 4-amino-3,5,6-trichloropyridine-2-carboxylic acid and 2.0 to 2.5 percent of excess NaOH.

A 3-L solution of 2% NaOH-1% NaCl was added to the circulation tank and was circulated at a rate of 18 L/min and a temperature of 35-38° C. through two undivided electrochemical cells in series. Each cell had a Hastelloy C anode (17.5 cm×5.6 cm) and an expanded silver mesh cathode (17.5 cm×5.6 cm). Only one of the two cells was controlled and monitored electrically. After normal anodization at +0.7 volts (V), the polarity of the cell was reversed to −0.5 V. After the electric current stabilized to less than 0.5 amp, this NaOH—NaCl solution was replaced with the previously prepared starting material solution which was circulated at a rate of 18 L/min and a temperature of 35-38° C. The silver cathode potential was set at −1.1 to −1.4 V relative to an Ag/AgCl (3.0 M Cl$^-$) reference electrode and the electrolysis was started. While recirculating the feed, 160 g of 50 percent by weight NaOH was slowly pumped into the recirculation tank over 6 hours to maintain the NaOH concentration at 1.5-3.0 percent excess. The current ranged from 0.5 to 12 amps.

No more anodization was needed after the electrolysis was started. After about 46 hours and 185,000 coulombs had been passed through the controlled cell, the electrolysis was terminated and the cell effluent was released to another 5 L flask and was neutralized with concentrated HCl. The total weight of the neutralized solution was about 3200 g. About 1000 grams of the solution was concentrated in vacuo to 750 g of crude concentrate. The concentrate was warmed to 85° C. while stirring and pH was adjusted to 0.8-1.1 with concentrated HCl over 30 min. The resulting slurry was cooled to ambient temperature and filtered. The filter cake was washed with 40 g of water three times, and dried in oven at 70° C. for 10 hours. The dried product weighed at 62 g with an assay of 95 percent desired product. High Pressure Liquid Chromatography analysis of the dried product indicated about 2 percent of the starting material remaining as an impurity.

Example 3

Preparation of
4-amino-3,6-dichloropyridine-2-carboxylic acid
(batch cell in presence of starting material, NaOH
and NaCl during activation)

To a 4-liter (L) flask was added 2370 grams (g) of hot water, 250 g of 50 percent by weight NaOH, 30 g of NaCl, and 350 g of wet 4-amino-3,5,6-trichloropyridine-2-carboxylic acid (80 percent). The solution was stirred for 30 minutes (min), filtered through a 1 micron polypropylene film, and transferred to a 5-L feed circulation tank. This solution weighed 3000 g and contained 9.3 percent 4-amino-3,5,6-trichloropyridine-2-carboxylic acid, 2.0 to 2.5 percent of excess NaOH, and 1.0 percent of NaCl.

This feed solution was circulated at a rate of 18 L/min and a temperature of 35-38° C. through the same two undivided electrochemical cells in series as in Example 1. After normal anodization at +0.7 volts (V), the polarity of the cell was reversed and the electrolysis was started. The cathode working potential on one of the two cells was controlled at −1.1 to −1.4 V relative to an Ag/AgCl (3.0 M Cl—) reference electrode. While recirculating the feed, 160 g of 50 percent by weight NaOH was slowly pumped into the recirculation tank over 6 hours to maintain the NaOH concentration at 1.5-3.0 percent excess. The current ranged from 0.5 to 10 amps.

No more anodization was needed after the electrolysis was started. After about 24 hours and 169,000 coulombs had been passed through the controlled cell, the electrolysis was terminated and the cell effluent was released to another 5 L flask and was neutralized with concentrated HCl. The total weight of the neutralized solution was about 3200 g. About 1000 grams of the solution was concentrated in vacuo to 750 g of crude concentrate. The concentrate was warmed to 85° C. while stirring and pH was adjusted to 0.8-1.1 with concentrated HCl over 30 min. The resulting slurry was cooled to ambient temperature and filtered. The filter cake was washed with 40 g of water three times, and dried in oven at 70° C. for 10 hours. The dried product weighed at 65 g with an assay of 95 percent desired product. High Pressure Liquid Chromatography analysis of the dried product indicated about 2 percent of the starting material remaining as an impurity.

What is claimed is:

1. An improved process for the preparation of a 4-amino-3-halopicolinic acid of Formula I

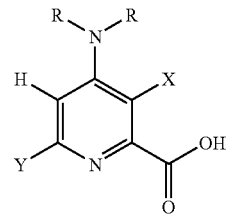

wherein
X represents Cl or Br,
Y represents H, F, Cl, Br or $C_1$-$C_4$ alkyl, with the proviso that when X is Cl, Y is not Br, and
R independently represents H or $C_1$-$C_4$ alkyl,
in which a direct or alternating electric current is passed from an anode to a silver cathode through a solution of a 4-amino-3,5-dihalopicolinic acid of Formula II

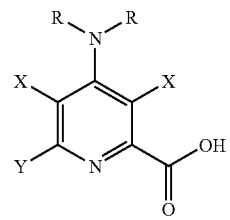

wherein
X, Y and R are as previously defined, and
wherein
both of X are either Cl or Br,
at a cathode potential of about −0.4 to about −1.7 volts relative to an Ag/AgCl (3.0 M Cl⁻) reference electrode, the improvement characterized by activating the cathode in the presence of the 4-amino-3,5-dihalopicolinic acid of Formula II, about 1 to about 4 wt % excess of alkali metal hydroxide and about 0.5 to about 4 weight percent of an alkali metal chloride, bromide or sulfate.

2. The process of claim 1 in which the silver cathode is activated by anodization in the presence of from about 0.5 to about 4 wt % NaCl, about 1 to about 4 wt % excess NaOH and about 1 to about 20 wt % 4-amino-3,5-dihalopicolinic acid of Formula II at a potential of at least 0.3 to about 0.7 volts followed by reverse polarization.

3. The process of claim 1 in which the 4-amino-3-halopicolinic acid of Formula I is aminopyralid and the 4-amino-3,5-dihalopicolinic acid of Formula II is picloram.

* * * * *